United States Patent [19]
Macovski

[11] 3,965,353
[45] June 22, 1976

[54] CROSS-SECTIONAL X-RAY EMISSION IMAGING SYSTEM

[76] Inventor: Albert Macovski, 4100 Mackay Drive, Palo Alto, Calif. 94306

[22] Filed: Dec. 6, 1974

[21] Appl. No.: 530,399

[52] U.S. Cl.................................. 250/336; 250/366; 250/369; 250/374
[51] Int. Cl.².............................................. G01T 1/00
[58] Field of Search ........... 250/361, 362, 363, 366, 250/369, 269, 270, 336, 374

[56] References Cited
UNITED STATES PATENTS

| | | |
|---|---|---|
| 2,946,889 | 7/1960 | Muench............................. 250/366 |
| 3,502,873 | 3/1970 | Woronowicz....................... 250/366 |
| 3,573,458 | 4/1971 | Anger............................. 250/369 X |
| 3,778,614 | 12/1973 | Hounsfield...................... 250/366 X |

*Primary Examiner*—Archie R. Borchelt

[57] ABSTRACT

A sheet beam x-ray source having energy components greater than 1.02 Mev is passed through an object under study. The emitted gamma rays due to pair production are measured using a positron-sensitive coincidence counting system on either side of the excited section. The location of each detected event is made using the positron information of each detector and the location of the excited section. An image is rapidly formed which is sensitive to the atomic number and density of materials in the cross section of the object.

11 Claims, 4 Drawing Figures

CROSS-SECTIONAL X-RAY EMISSION IMAGING SYSTEM

BACKGROUND OF THE INVENTION

1. Field of the Invention

This invention relates to x-ray cross-sectional imaging systems. In a primary application the invention relates to medical imaging systems for providing a cross section representing the amount of an administered material.

2. Description of Prior Art

Cross-sectional imaging systems using x-rays have recently made a significant impact on medical diagnosis. These instruments, made by EMI of England and ACTA in the United States, are used primarily in brain studies. Their relatively long scanning time, of approximately five minutes, limits their use to regions, such as the head, which can be immobilized. Regions involved with respiratory or cardiovascular motions would have a severe loss of resolution due to smearing. The principal reason for the long scanning time is the requirement that the x-ray projections be made over a large number of angles. In addition to the long scanning time, a significant and costly time interval is required to compute the reconstructed image from the projection data. A description of the EMI system is given by J. Ambrose and G. N. Hounsfield in the *British Journal of Radiology*, Vol. 46, 1973.

These cross-sectional imaging systems can be used to image both density distributions and the presence of an administered contrast material which is selectively taken up in specific areas of the body. Nuclear medicine procedures are also used to image the takeup of materials. In this case, these materials have been radioactively labeled. One method of radioactive labeling involves positron annihilation where a pair of gamma rays are produced each having an energy of 0.51 Mev and travelling in equal and opposite directions. In the case of positron annihilation, the nuclear medicine positron sensitive cameras can measure the line along which the event occurred. Two cameras are positioned to determine the position coordinates of each of the emitted gamma rays. Using a coincidence detection system, when each detector records an event at approximately the same time, the recorded lateral positrons are used to determine the line of occurrence. The determination of the depth dimension is not available. Some attempts have been made to use the time of flight to each detector. However, for 1 cm. resolution in depth, better than 40 picosecond temporal resolution would be required which is extremely difficult to obtain. Another problem with all nuclear medicine procedures, whether or not positron annihilation is used, is the relatively large dosage of radiation given to the patient because of the relatively long half-lives of the radioactive materials.

SUMMARY OF THE INVENTION

An object of this invention is to provide x-ray cross-sectional imaging apparatus which will result in the generation of cross-sectional images in significantly reduced time so as to allow for the study of moving structures.

It is also an object of this invention to provide x-ray cross-sectional images without requiring extensive computer facilities.

It is also an object of this invention to provide x-ray cross-sectional images with a minimum number of projection angles.

It is a further object of this invention to provide x-ray cross-sectional images which represent the amount of an administered contrast material.

BRIEF DESCRIPTION OF THE DRAWINGS

For a more complete disclosure of the invention, reference may be made to the following detailed description of several illustrative embodiments thereof which is given in conjunction with the accompanying drawings, of which.

DESCRIPTION OF THE PREFERRED EMBODIMENT

Figure 1:
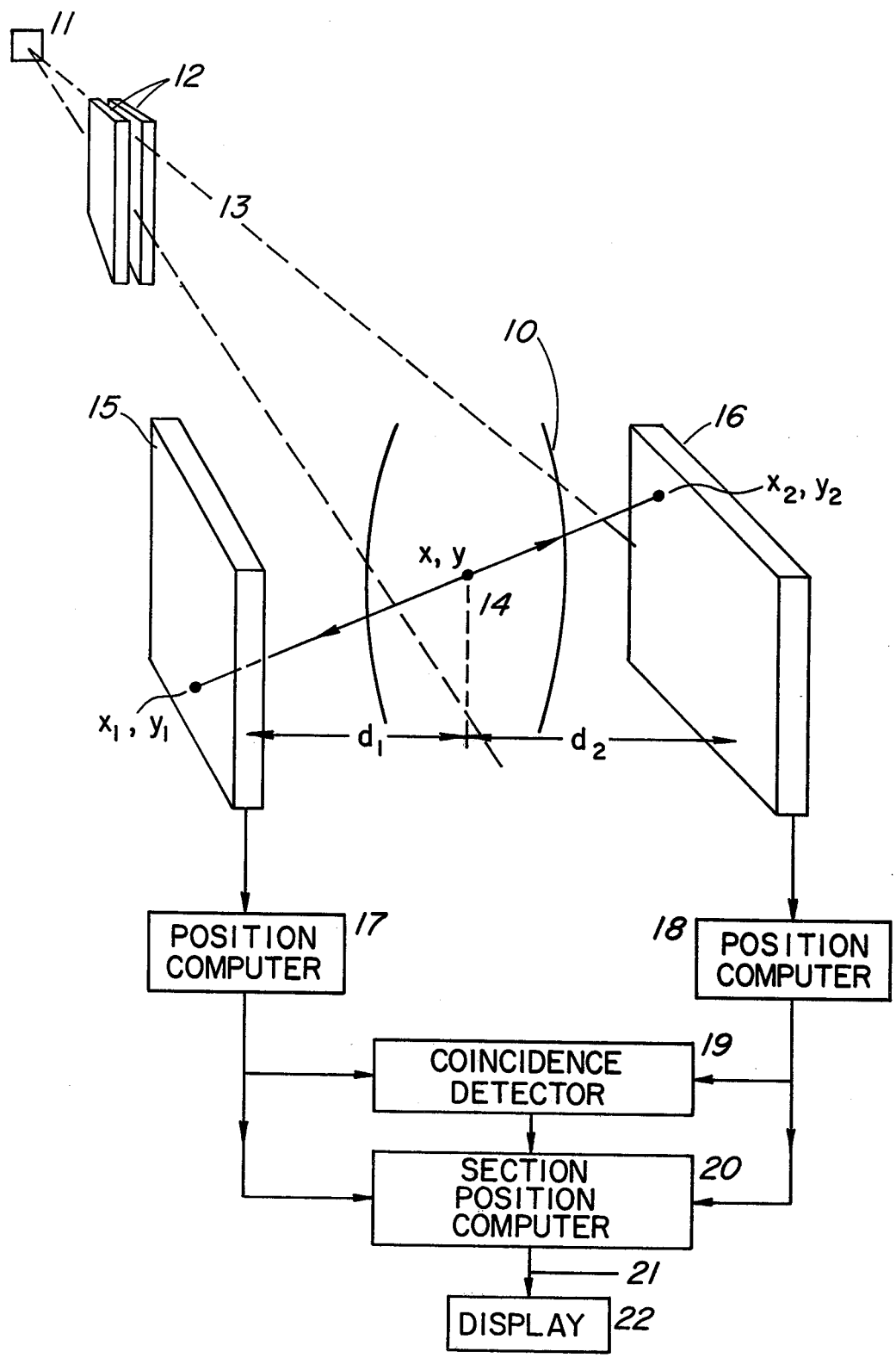
FIG. 1 illustrates an embodiment of the invention using two positron sensitive detectors.

An understanding of the broad aspects of the invention may best be had by reference to FIG. 1 of the drawings. An object 10, for example the human body, is being studied using x-rays. An x-ray source 11 produces a planar or sheet beam 13. The x-ray source, in this system, must contain energy components greater than 1.02 Mev so as to provide pair production. For example, the source can be an x-ray tube with an accelerating voltage greater than 1.02 Mev. Another alternative source is an isotope having at least one emitted energy level greater than 1.02 Mev. The exact energy of the source is a compromise between a number of considerations. If a relatively low energy is used, the efficiency of pair production is relatively low. If, however, a very high energy source is used, the positron annihilation can take place a considerable distance from its initial production. This phenomenon reduces the resolution of the system since the detectors do not accurately measure the true region where the interaction occurs. An energy of about 2 Mev would appear to be a reasonable compromise between a resolution of less than 5 millimeters and a reasonable efficiency of pair production.

The sheet beam 13 results in pair production at many regions of the plane including point 14 in object 10. Two gamma rays are emitted in exactly opposite directions. These are detected by gamma-ray detectors 15 and 16 which are position indicating gamma ray detectors such as the Anger camera, proportional wire chamber or the detector array used with the Baird Atomic System 70. The Anger camera is commercially available and consists of a scintillating crystal followed by an array of photomultipliers. The centroid of the photomultiplier outputs is used to compute the $x$ and $y$ positions. Position computers 17 and 18 thus compute point $x_1,y_1$ from detector 15 and point $x_2,y_2$ from detector 16. To insure that the recorded event in both cameras is due to pair production, coincidence detector 19 is used. As is conventionally done in positron annihilation imaging, a coincidence detector is used which produces an output pulse only when input pulses are present at both detectors. When both pulses are present, the coincidence detector sends a pulse to section position computer 20. This computer calculates the position 14, noted by coordinates $x,y$, where the pair production event occurred. This computer 20 takes as inputs the individual detector positions $x_1,y_1$ and $x_2,y_2$ and the distances of each detector from the section excited by the sheet beam, $d_1$ and $d_2$. Using simple geometric relationships the $x,y$ coordinates are calculated as $$x = \frac{d_2x_1 + d_1x_2}{d_1 + d_2} \text{ and } y = \frac{d_2y_1 + d_1y_2}{d_1 + d_2}$$

The $d_1$ and $d_2$ positions can be manually set in computer 20 or alternatively they can be automatically applied using potentiometers driven by the position of source 11 and its associated collimator 12. The relatively simple computation shown above can be implemented in analog or digital form. A simple analog computer for this function is a potentiometer with a voltage representing $x_1$ on one end and a voltage representing $x_2$ at the other end. The arm of the potentiometer is placed at the relative position of the sheet beam between the two detectors so that the voltage at the arm directly indicates position $x$. An identical system is used to calculate $y$ using $y_1$ and $y_2$. The calculated values indicated by signal 21 are then applied to the deflection system of display 22 which places a dot in the correct position.

Since pair production generation increases as the square of the atomic number, the resultant cross-sectional image on display 22 will be dominated by high atomic number materials. This is of particular value in medical diagnosis involving contrast materials. For example, in a cardiovascular study, iodine is administered into the heart and circulatory system. This system should be sensitive enough to use an intravenous dose of iodine rather than requiring the use of catheters with their associated dangers. The fact that the x-ray source and detectors are not moved or scanned, as they are in the EMI and ACTA scanners, allows the study to be done rapidly. This is essential in cardiovascular studies where extensive motion is taking place. Another important area is the diagnosis of tumors by their selective uptake of relatively high atomic number materials. This is presently widely done in nuclear medicine procedures. In nuclear medicine, however, the study is limited to materials that can be conveniently labeled and the radiation dosage is relatively high. In addition, the imaging procedure does not indicate individual cross sections but produces a superposition of all sections in the object. In contrast, the system indicated here does not require radioactive labelling, is relatively low in radiation and images individual cross sections.

In addition to the desired pair production, undesired Compton scattering will also occur. Much of this will be eliminated as a result of the coincidence detector 19. Most of the remaining Compton scattered photons can be eliminated by using energy selection in the gamma-ray detectors 15 and 16. Using pulse-height analysis only those gamma rays having energies in the immediate vicinity of 0.51 Mev will be accepted. This will serve to eliminate most scattered photons which are not eliminated by the coincidence detector.

Energy selection can be used as the sole mechanism for selecting the 0.51 Mev photons which are generated by pair production. In this case coincidence detection would not be used. Only one position sensitive gamma ray detector is required such as 15, with 16 eliminated. An imaging structure such as a multiple-hole collimator or a pin hole is placed between the detector 15 and the object 10 in a manner identical with that of the conventional Anger camera. If a parallel hole collimator is used, the $x_1,y_1$ positrons of the detected gamma rays, appropriately energy selected, will directly represent the desired $x,y$ points of the emitted gamma rays. Thus further computation is not necessary and the $x_1,y_1$ deflection values are applied directly to display 22. If a pin hole is used, the $x_1,y_1$ values will have to be scaled by the ratio of the distance of the pin hole to the illuminated cross section divided by the distance of the pin hole to detector 15 to compute the desired $x,y$ points. Both the parallel hole collimator and pin hole are relatively inefficient in that they collect a small portion of the emitted gamma rays. Thus two gamma-ray detectors plus a coincidence detector is much preferable from an efficiency standpoint since attenuating imaging structures are not required.

In FIG. 1 two position sensitive gamma-ray detectors 15 and 16 are shown. In the interest of economy, one of the detectors, for example detector 16, can be made a point detector at a fixed position. This method is simpler although considerably less efficient since only those photons impinging on this point detector will be used. For example, a single small crystal and photodetector can be placed at a position corresponding to $x_2 = 0$ and $y_2 = 0$ on detector 16. When a pair production event excites the point, the corresponding $x_1,y_1$ position can be used to directly indicate the position of the event using the equation $$x = x_1 \frac{d_2}{d_1 + d_2} \text{ and } y = y_1 \frac{d_2}{d_1 + d_2}$$

Thusfar, in the general method shown in FIG. 1, no use has been made of the transmitted sheet beam. This information can be used to provide additional high resolution information for improving the image. The image as formed by the system of FIG. 1 will have a resolution of approximately 5 mm because of the performance of existing position-sensitive detectors. This resolution can be improved by using a detector array to measure the transmitted radiation. The EMI and ACTA scanners reconstruct cross-sectional images using information derived from projections made at 180 different angles. However, using projection information from just a few angles, the image obtained by the system of FIG. 1 can be enhanced. Each projection, when Fourier transformed, becomes one line of the two-dimensional Fourier transform of the desired cross-section. Thus one method of reconstruction involves first interpolating between known lines in the Fourier transform plane and then inverse transforming to obtain the reconstruction. A system of this type is described in a paper entitled "Computer Aided Transverse Body-Section Radiography" by T. M. Peters, et al., in the *British Journal of Radiology*, volume 46, 1973, on pages 314–317.

Another widely published method of reconstruction is known as the convolution method. In this method each projection is convolved with a fixed function and then back-projected across the entire reconstruction plane. This fixed function undoes the smearing effect caused by the superposition of each back projection and provides the desired reconstruction. This convolution method is explained in a paper entitled, "General Views on 3-D Image Reconstruction and Computerized Transverse Axial Tomography" by Z. H. Cho in the *IEEE Transactions on Nuclear Science*, volume NS-21, June 1974 on pages 44–71.

Figure 2:
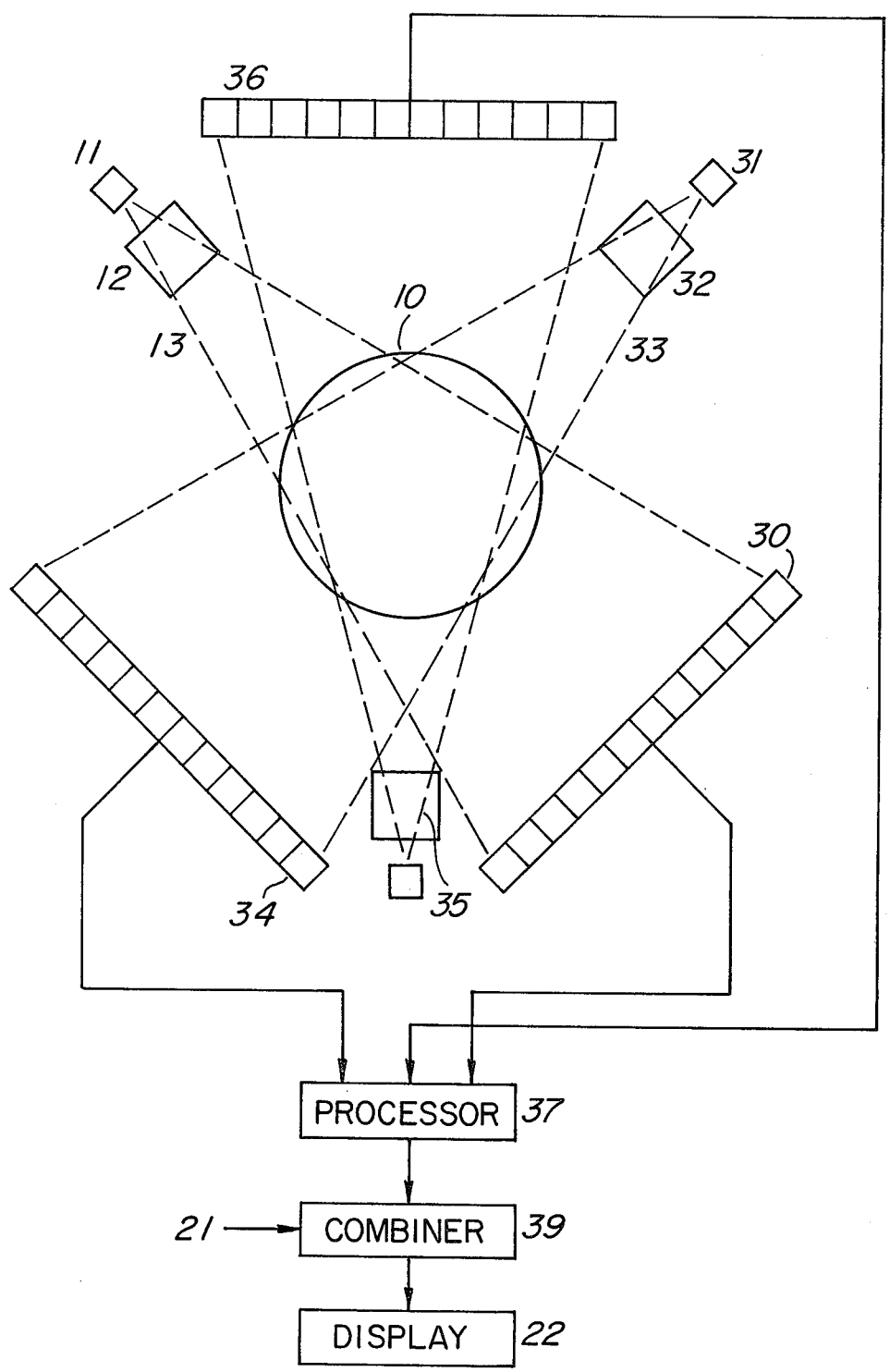
FIG. 2 illustrates an embodiment using multiple x-ray sources with transmission detectors.
Figure 3:
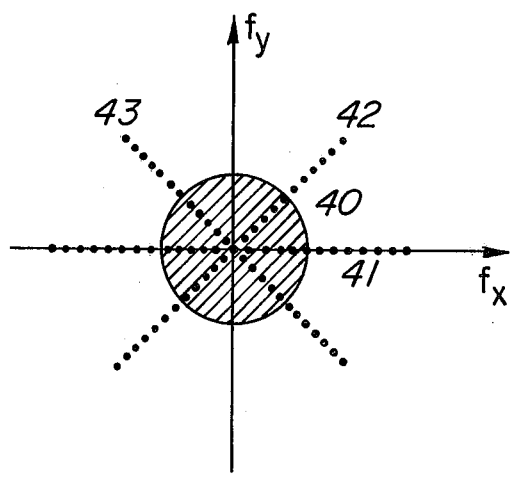
FIG. 3 illustrates the Fourier transform of the acquired data in the embodiment using multiple x-ray sources.

Either of these methods can be used to enhance the system of FIG. 1. FIG. 2 illustrates a representative multiple-source x-ray system for obtaining three projections of the cross section of object 10 under study. This is essentially an orthogonal view of the system of FIG. 1 with the position-sensitive detectors, 15 and 16, omitted for purposes of clarity. They would be placed above and below the cross-section in object 10. The multiple excitation of the cross-section by sheet beams 33 and 35, in addition to beam 13 has no profound effect on the pair production in the cross section other than to increase the output. Thus the position-sensitive detectors will receive three times as many photons. The significant effect of the configuration of FIG. 2 is the measurement of the transmission of the cross section at three angles separated by approximately 120°. Thus the transmission of the cross section of object 10 by sheet beam 13 is measured by linear detector 30. This linear detector is an array of gamma-ray detectors such as scintillating crystals with their associated photodetectors or a multiwire proportional chamber consisting of a gas such as Xenon with wires providing an electrostatic field. Each detector in the linear array produces an output corresponding to the projection through the cross section in that particular direction. Similarly sheet beam 33 is formed by source 31 and collimator 32, transmitted through the cross section in object 10 and collected by linear detector array 34. Sheet beam 35 is similarly formed with the transmitted beam collected by linear detector array 36. The outputs from each of the detectors are collected and processed in the manner previously described. FIG. 3 is a diagram indicating the two-dimensional information which has been collected. The two-dimensional Fourier transform of the cross section under study is shown. The circular shaded region 40 indicates the lower spatial frequency information which is collected by the position-sensitive detectors shown in FIG. 1. The resolution limits of these detectors determine the highest spatial frequency. The dotted lines, 41, 42, and 43 are the information collected by the three transmission detectors 30, 34 and 36 in FIG. 2. As was previously pointed out, each transmission measurement represents a line in the two-dimensional Fourier space. The processor 37 in FIG. 2 gathers this information and processes it in a manner to enhance the resolution of the original image reconstruction of FIG. 1. One method of processing is the use of interpolation so as to fill in the sparse data outside of the circle 40 in FIG. 3. Conventional interpolation methods can be used to fill in an annulus outside of circle 40 using both the line information 41, 42 and 43, and the information within circle 40. The processor 37 can then take the inverse transform of this annulus and generate the higher frequency information 38. This signal is then added to the lower resolution information from the pair production detectors in FIG. 1 indicated by signal 21 in combiner 39. The output is appropriately applied to display 22.

Processor 37 can also be used to provide the alternate convolution reconstruction system previously discussed. Using a digital or analog computer each projection can be convolved with the known function. As previously described, this function is determined by the number of projections used. These convolved projections, as is well-known in the literature, are back projected across the entire reconstructed image of the cross section. Thus processor 37 provides the convolving, back projection and summation functions. The high frequency components of the sum of the back projections are then added to signal 21 in combiner 39 and applied to display 22. The convolution function itself, in processor 37, can provide the high frequency components only and thus avoid the use of high-pass filters in processor 37.

In the method of FIG. 2 a plurality of sheet beam sources and associated transmission detectors are used simultaneously. In studies which do not involve motion, where a relatively long time can be used to acquire the data, a single source and detector array can be used to collect the data in sequence. For example, source 11 with its collimator 12, along with detector 30, can be rotated about an axis which is approximately in the center of the cross section under study. The transmission data at a number of angular positions in sequence, is applied to processor 37 where the processing takes place exactly as previously described. For example, transmission detector 30 can be rotated so as to sequentially occupy the positions of transmission detectors 34 and 36 in FIG. 2, with the associated sheet beam 13 correspondingly rotated. Processor 37 must include sufficient data storage to store the information at each angular position and process it as previously described.

Figure 4:
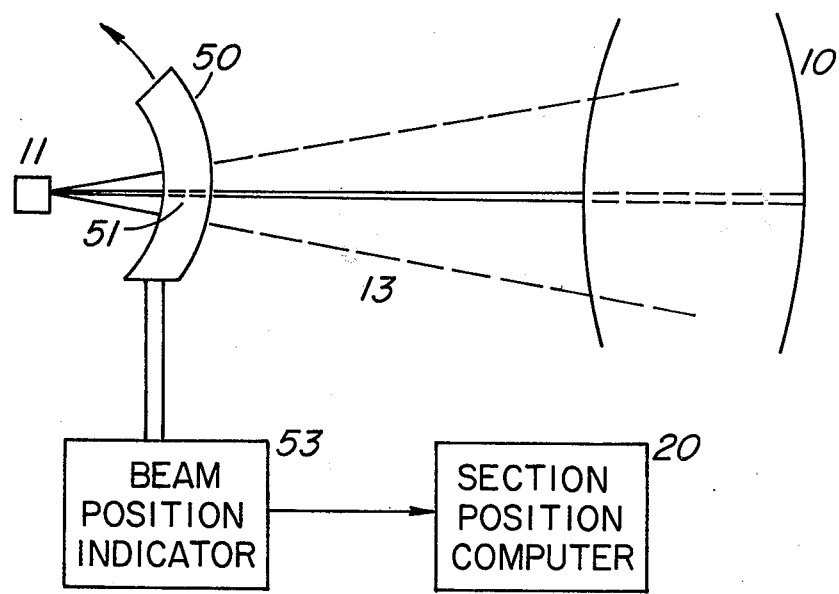
FIG. 4 illustrates an embodiment using a scanned pencil beam.

In FIGS. 1 and 2 the x-ray sheet beams, 13, 33, and 35 were supplied by a continuous x-ray source and a collimator. An alternate source of a sheet beam involves dynamically translating or sector scanning a pencil beam so that the envelope or raster of the scanning beam becomes a sheet beam. One example of this is shown in FIG. 4 where source 11, as before, produces a divergent beam of x-rays. Beam former 50 is an x-ray shield with aperture 51 which allows a pencil beam from source 11 to pass through. Beam former 50 is oscillated or rotated in the plane of the figure about source 11 as an axis. Thus aperture 51 intercepts different parts of the diverging beam and creates the effect of an oscillating or sector scanned beam. The extent of the scanned beam forms sheet beam 13. Many other methods exist for creating a scanned beam which forms a sheet beam. For example source 11, with a beam forming aperture, can be translated to form a scanning beam.

The disadvantage of a scanned beam is that a relatively small fraction of the source capability is being used as compared to the sheet beam collimators of FIGS. 1 and 2. The advantage is that the various detectors are relieved of some of their position sensitivity requirements since one dimension is now presented as a time sequence. For example, if the sheet beam 13 of FIG. 1 is formed as a pencil beam translated in the $y$ direction, the pair production detectors 15 and 16 will only have to be position sensitive in the $x$ direction. The $y$ direction is known as a result of the known time at which the beam occupies each $y$ position. Thus the $y$ coordinate of the emission becomes a known function of time and only $x$ need be calculated. This can greatly simplify the construction of these detectors. Thus beam position indicator 53 is connected to moving beam former 50. This indicator can simply be a potentiometer driven by the rotation of 50. The beam position indicating signal is connected to section position computer 20 so as to supply one dimension of the position computation with the outputs of detector 15 and 16, as before, supplying the other dimension. Similarly the transmission detectors 30, 34, and 36 in FIG. 2 can be continuous scintillating crystals having one long photodetector rather than requiring an array of photodetectors. The required transmission information along each point of the detector will now be a known function of time at the detector output since the beam 52 is transmitted through a different portion of the cross section of object 10 at different times. Thus the output of beam position indicator 53 would also be used in processor 37 to derive the transmission information.

What is claimed is:

1. Apparatus for producing an image of a cross section of an object comprising:
   means for illuminating the cross section with x-rays having energies greater than 1.02 Mev;
   position-sensitive detector means for detecting gamma rays emitted from the illuminated cross section due to pair production and producing a plurality of detected position signals;
   means for computing the point of emission of the gamma rays in the illuminated cross section using the detected position signals and producing a gamma-ray emission signal; and
   means for displaying the gamma-ray emission signals whereby an image of the cross section will be formed.

2. Apparatus as recited in claim 1 wherein the position-sensitive detector means includes two position-sensitive gamma-ray detectors with each at a known distance on either side of the cross section and a coincidence detector connected to the outputs of both position-sensitive gamma-ray detectors for accepting only those events detected simultaneously by the two position-sensitive gamma-ray detectors.

3. Apparatus as recited in claim 2 wherein one of the two position-sensitive gamma-ray detectors is a point detector whereby only gamma-rays at a specific region are detected, thus defining their position.

4. Apparatus as recited in claim 2 wherein the means for computing the point of emission of the gamma rays in the illuminated cross section uses the detected position signals from both position-sensitive gamma-ray detectors and the known distances of each from the cross section in a linear relationship.

5. Apparatus as recited in claim 1 wherein the means for illuminating the cross section includes an x-ray source having an emitted beam with energies greater than 1.02 Mev, a collimator having a slit opening positioned in the beam of the x-ray source to attenuate all of the x-rays in the emitted beam other than those passing through the slit opening whereby a sheet beam is formed which illuminates the cross section of the object.

6. Apparatus as recited in claim 1 wherein the means for illuminating the cross section includes an x-ray source having an emitted beam with energies greater than 1.02 Mev, an x-ray shield having an aperture positioned in the beam of the x-ray source to attenuate all of the x-rays in the emitted beam other than those passing through the aperture and forming a pencil beam, and means for moving the aperture to successively illuminate the cross section with the scanning pencil beam.

7. Apparatus as recited in claim 6 wherein the position-sensitive detector means provides position signals in a direction normal to the motion of the pencil beam and including means for deriving the beam position to provide the position information in the beam scanning direction.

8. Apparatus as recited in claim 1 wherein the position-sensitive detector means includes an energy selective pulse-height discriminator for rejecting those detected gamma rays whose energies are not approximately 0.51 Mev.

9. Apparatus as recited in claim 1 wherein the means for illuminating the cross section includes a plurality of x-ray sources each having its beam collimated into a sheet beam and illuminating the cross section from different angles and further comprising:
   a plurality of linear detectors for detecting the intensity along the sheet beams transmitted through the cross section from different angles and forming a plurality of transmission projection signals;
   means for processing the plurality of transmission projection signals for obtaining density data of the cross section; and
   means for displaying the density data of the cross section in combination with the gamma-ray emission signals.

10. Apparatus as recited in claim 9 wherein the means for displaying the density data of the cross section in combination with the gamma-ray emission signals includes means for removing the high spatial frequency components of the density data and adding them to the gamma-ray emission signals.

11. Apparatus as recited in claim 1 including:
   a linear detector for detecting the intensity of the x-rays transmitted through the cross section and forming a transmission projection signal;
   means for rotating the linear detector and the means for illuminating the cross section around the cross section to form a plurality of transmission projection signals at a plurality of angles;
   means for processing the plurality of transmission projection signals for obtaining density data of the cross section; and
   means for displaying the density data of the cross section in combination with the gamma-ray emission signals.

* * * * *